(12) United States Patent
Stanley et al.

(10) Patent No.: US 8,603,771 B2
(45) Date of Patent: Dec. 10, 2013

(54) CAPTURE OF MICRO-ORGANISMS

(75) Inventors: Christopher John Stanley, Cambridge (GB); Stuart Mark Wilson, London (GB)

(73) Assignee: Microsens Medtech Limited, London (GB)

( * ) Notice: Subject to any disclaimer, the term of this patent is extended or adjusted under 35 U.S.C. 154(b) by 0 days.

(21) Appl. No.: 13/813,637

(22) PCT Filed: Jun. 29, 2011

(86) PCT No.: PCT/GB2011/051225
§ 371 (c)(1),
(2), (4) Date: Jan. 31, 2013

(87) PCT Pub. No.: WO2012/001407
PCT Pub. Date: Jan. 5, 2012

(65) Prior Publication Data
US 2013/0171689 A1    Jul. 4, 2013

(30) Foreign Application Priority Data
Jul. 2, 2010  (GB) .................................. 1011152.4

(51) Int. Cl.
*C12Q 1/04* (2006.01)
*C12Q 1/24* (2006.01)

(52) U.S. Cl.
USPC .......................... 435/34; 435/252.4; 210/800

(58) Field of Classification Search
None
See application file for complete search history.

(56) References Cited

U.S. PATENT DOCUMENTS 7,166,425 B2    1/2007   Madonna et al.

FOREIGN PATENT DOCUMENTS

| JP | 2001-112497 | 4/2001 |
| WO | 95/32304 | 11/1995 |
| WO | 2008/065047 | 6/2008 |
| WO | 2008/072242 | 6/2008 |
| WO | 2009/046191 | 4/2009 |
| WO | 2009/086343 | 7/2009 |
| WO | 2011/117201 | 9/2011 |
| WO | 2011/117202 | 9/2011 |

OTHER PUBLICATIONS

International Search Report dated Nov. 23, 2011 in corresponding International Patent Application No. PCT/GB2011/051225.
Ji Yeong Won et al., "Bacteria adsorption on hydrophilic surfaces for the sensitive detection of pathogenic bacteria using a single tube chamber system," Biosensorsand Bioelectronics, vol. 26, pp. 1763-1767 (2010).
S. Wilson et al., "Concentration of *Mycobacterium tuberculosis* from sputum using ligand-coated magnetic beads," Int. J. Tuberc. Lung Dis., vol. 14, No. 9, pp. 1164-1168 (2010).

*Primary Examiner* — John S Brusca
*Assistant Examiner* — Sharon M Papciak
(74) *Attorney, Agent, or Firm* — Pillsbury Winthrop Shaw Pittman LLP

(57) ABSTRACT

Micro-organisms, including fungi, viruses and bacteria such as *Mycobacteria* and/or fragments of micro-organisms such as cell wall components present in an aqueous liquid are captured to a solid surface by adding to the liquid a sufficient quantity of a water soluble polymer in the presence of the solid surface to displace the micro-organisms and/or fragments from the liquid to the solid surface. The surface may be provided by a bead. The water soluble polymer may be polyethyleneglycol or polyvinylpyrrolidone.

20 Claims, No Drawings

CAPTURE OF MICRO-ORGANISMS

CROSS REFERENCE TO RELATED APPLICATIONS

This application is the National Phase entry of PCT/GB2011/051225, which claims priority to Great Britain Patent Application No. 1011152.4, filed Jul. 2, 2010. The content of this application is incorporated herein by reference in its entirety.

The present invention relates to methods of capturing micro-organisms from suspension, and also to their subsequent detection and/or identification.

BACKGROUND

In many applications it is desirable to capture a microorganism from a suspension thereof as a first step allowing one subsequently to conduct further work on the micro-organism, e.g. to concentrate a microorganism into a small volume free of impurities and contaminants, for diagnostic purposes for example. The microorganisms may initially be present in a large volume sample material, such as sputum, blood, dispersed food or potable water. Concentration into a small volume that is free of sample contaminants optimises sensitivity and removes inhibitors in diagnostic procedures, such as microscopy, immunoassay or nucleic acid amplifications processes such as PCR. Existing methods to achieve microorganism concentration include the use of paramagnetic beads coated with a microorganism-specific antibody; the beads can be used to specifically capture microorganisms from a sample allowing their subsequent detection by various methods (U.S. Pat. No. 7,166,425).

In some applications, however, the capture conditions may not be suitable for an antibody-based system: for example, in the capture of mycobacteria from sputum that has been thinned with sodium hydroxide and which remains at a high pH which would inactivate antibodies. In these and other circumstances of harsh conditions antibody capture cannot be used. In addition, in other applications it may be desirable to capture any microorganism that may be present in the sample. For example, in sepsis it is important to capture any bacterial or fungal cells that might be present in the blood so that a diagnosis can be made. Similarly, in testing blood products, such as in platelet screening, it is important to know if the blood products (in this case platelets) are contaminated with any microorganism at all. Under such circumstances it would be hard to do this with an antibody-based approach as antibodies tend to be organism or species-specific.

Methods that are not based on antibodies have been described. JP2001112497 describes removing *Mycobacteria* from an alkali decontaminated liquid by precipitating calcium phosphate therein, the precipitate presumably carrying down the bacteria as it forms. WO 2009/086343 describes the use of a carbohydrate-coated surface together with a biotin binding protein and an amphiphilic glycoside of a steroid or triterpene to bind microorganisms. WO28072242A2 describes a polymeric matrix derivatised with amino acids as a binding surface and WO29046191A2 describes the use of diatomaceous earth particles coated with various metallic or inorganic surfaces to achieve the same result. These methods are more generic than antibody-based approaches but are not truly generic in that some bacterial species are captured better than others and some species or strains of bacteria may not be captured at all. In addition, these methods have not been shown to capture fungi.

These issues are a consequence of relying on the surface property of the binding matrix, which is necessarily limited in nature, to bind bacteria that may have a diverse outer cell wall structure. In this invention, we describe a novel approach that is less dependent in the nature of the surface matrix and has been shown to work with gram positive and gram negative bacteria and fungi in addition to *Mycobacteria* which tend to have a uniquely hydrophobic cell wall.

BRIEF DESCRIPTION OF INVENTION

We have now found that it is possible to use a water soluble polymer to cause suspended micro-organisms to be deposited onto a solid surface. The method also operates to cause sedimentable and non-sedimentable fragments of micro-organisms to deposit onto a solid surface. Whilst it has been known for some time that proteins in solution can be caused to precipitate by addition of water soluble polymers such as polyethylene glycol (PEG) or dextran, no solid surface being involved, these findings in respect of micro-organisms and fragments thereof are unexpected.

WO95/32304 uses an aqueous two-phase polymer separation system to selectively enhance the number of target micro-organisms with respect to background flora, but does not suggest capture to a solid surface.

The present invention accordingly now provides a method of capturing onto a solid surface micro-organisms and/or fragments thereof in an aqueous liquid, comprising adding to said liquid a sufficient quantity of a water soluble polymer in the presence of said solid surface to displace said micro-organisms and/or fragments from the liquid to the solid surface.

Alternatively expressed, the process may comprise providing together a solid surface and an aqueous liquid containing micro-organisms and/or fragments thereof and a water soluble polymer so as to displace said micro-organisms and/or fragments thereof from said liquid onto said solid surface.

Fragments of micro-organisms which can be captured in this way include sedimentable fragments that could be centrifuged to deposit from the liquid using centrifugation at 4,000×g for 20 min which is the speed that is normally used to sediment bacteria. Surprisingly, the method also works to capture fragments, which may include soluble proteins or other soluble cell components, that cannot be caused to deposit under such centrifugation conditions and which may be termed non-sedimentable.

The concentration of the added water soluble polymer in the aqueous liquid may be freely adjusted according to the nature of the polymer so as to produce the desired displacement of the micro-organism and/or fragments from suspension or solution in the liquid to be deposited on the solid surface. Optionally, the polymer concentration is from 2 to 30% w/v, preferably 5 to 20% w/v, more preferably 7 to 15% w/v, most preferably about 10% w/v. These concentrations are particularly suitable for use with PEG or polyvinylpyrrolidone (PVP) as the polymer.

Preferably, the water soluble polymer is a non-ionic hydrophilic polymer. It may for instance be a dextran, a PVP or a PEG. The PEG may be polydisperse in molecular weight or monodisperse, may be branched or straight chain and may be of a star type.

Suitably, the water soluble polymer has a weight average molecular weight of from 200 to 100,000. It may for instance have a molecular weight of from 1,000 to 20,000, more preferably 5,000 to 13,000, e.g. about 8000. These molecular weights are particularly suitable in the case of PEG or PVP.

Binding of the micro-organism to the solid surface may be enhanced by the use of high ionic strength conditions. Suitably, the ionic strength of the aqueous liquid is raised by the addition of a water soluble inorganic salt to from 150 mM to 6M, more preferably from 0.25 to 0.75M, e.g. 0.5M.

Many different salts can be added to the solution to achieve a high ionic strength, for example, ammonium sulphate, ammonium chloride, magnesium sulphate, magnesium chloride but sodium chloride is preferred.

The binding to a surface can be performed in conditions of high or low pH in the range 1-14. Where the micro-organism is *Mycobacteria*, a high pH such as from 9 to 14 may be preferred in order to kill or reduce the ability to reproduce of other kinds of bacteria that may be present.

In addition, the binding to a surface can be performed in the presence of a detergent which can include ionic (such as sodium dodecylsulphate) or non-ionic (such as Tween20 and Triton X100) detergents.

It is preferred that the solid surface has a high specific surface area and hence, preferably the solid surface is provided by beads. The term 'beads' includes but is not limited to insoluble particles that are spherical or irregular in nature and of size ranging from 0.1 micron to 5 mm in size.

A method according to the invention may further comprise separating said solid surface from said liquid.

There are well established physical approaches for generic concentration of micro-organisms, for example: filtration of a sample where the cells become trapped either on the surface of a size exclusion filter or within the structure of a depth filter; or centrifugation in which the cells are sedimented. Although these methods are useful for preparing a concentrated suspension of micro-organism that is free of sample contaminants they also have disadvantages. In the filtration approach it is simple (subject to the inherent disadvantages of filtration) to capture whole organisms of defined size but fragments of organisms of undefined size are more difficult to capture in this way. In addition, it may be difficult to recover the micro-organisms after they have been trapped by the filter and, when recovered by an elution or reverse flow washing process the micro-organism may disadvantageously be present in a relatively large fluid volume. Again, centrifugation can be used to concentrate whole organisms but fragments of organisms may be non-sedimentable at the speed and time used. In addition, centrifugation requires an instrument and also this step cannot easily be incorporated into an automated procedure for microorganism concentration and detection. Additionally, after centrifugation it is difficult to resuspend reliably the sedimented pellet containing the microorganisms in the desired small volume, often larger volumes are required to ensure full dispersal of the pellet in the tube.

Accordingly, it is preferred that the nature of the solid surface on which the micro-organisms and/or fragments are received is such that the solid surface can be separated from the suspending liquid without the use of filtration or centrifugation. It is therefore preferred that the beads are attractable to a magnet for separation or are sufficiently dense that they can be separated by sedimentation even if the polymer containing liquid is quite viscous. Therefore, it is preferred that said beads are paramagnetic or have a density sufficiently above the liquid that they sediment without centrifugation, e.g. above 2.0 g/ml, more preferably above 3.0 g/ml. Alternatively, they may have a density sufficiently below that of the liquid that they will separate to float on the liquid, e.g. hollow beads, which may be of glass. Such buoyant beads may have a density below 0.8 g/ml, e.g. from 0.4 to 0.7 mg/ml.

Suitable dense bead materials, or bead core materials, are aluminium oxide, silicon carbide, silicon nitride, titanium carbide, iron oxide (such as magnetite) and glass.

The solid surface may be of a polymer having positively charged or negatively charged surface groups. Examples of suitable surface groups are amine, quaternary ammonium, carboxylic acid, sulphonic acid, or sulphate groups. Suitable materials include dextran sulphate and poly(diallyldimethylammonium chloride) (pDADMAC).

The bead may be of one material throughout or may have a core bearing a surface coating. We have found that the use of particles presenting a surface of magnetite, uncoated magnetite particles, has particular advantages. Such particles are ferromagnetic (in the broad sense, including ferrimagnetic) and so are readily separated from liquid medium and micro-organisms and/or fragments thereof are readily caused to adhere to the surface of such particles by the presence in liquid medium of soluble polymers. Moreover, the removal of liquid medium containing such polymers and its replacement by a liquid in which such polymers are not present provides a ready means of removing the captured materials from the solid surface.

A method according to the invention may further comprise eluting said micro-organisms and/or fragments from said solid surface after separation thereof from said liquid. The elution can be performed under a wide range of conditions, for instance in buffers with a range of salt concentrations from 150 mM to 6 M. In addition, non-ionic, ionic or zwitterionic detergents such as Tween20, Triton X-100, CTAB, sarkosyl or SDS can be included to aid elution from the bead surface.

In order to effect a concentration of the micro-organisms and/or fragments, it is preferred that the micro-organisms and/or fragments are eluted from the solid surface into a volume of liquid which is less than the volume of the liquid in which the micro-organisms and/or fragments were originally suspended by a factor of at least 2, e.g. at least 4.

A method of the invention may further comprise detecting the micro-organisms and/or fragments which were captured onto the solid surface. This may be performed after elution from the solid surface or whilst the micro-organisms and/or fragments remain on the solid surface. It may be performed either after removing the aqueous liquid from the solid surface or whilst it still remains. For instance, after capturing the micro-organisms and/or fragments to beads, a labelled binding agent such as an antibody specific for the micro-organisms and/or fragments or auramine stain may be added and the liquid may be run through a cell sorter apparatus to detect labelled beads.

Beads or other forms of solid surface bearing micro-organisms and/or fragments may be stained with a micro-organism stain, either directly or after culturing the organism to increase the number thereof. For instance, *Mycobacteria* may be revealed by the use of an acid fast stain for visualisation. Other forms of detection such as nucleic acid amplification techniques (e.g. PCR), detection of metabolites, antibody based detections such as ELISA for the micro-organisms themselves or cell components thereof may be used. One suitable ELISA method for detecting *Mycobacteria* and/or fragments is for instance disclosed in GB1004710.8. Capture methods described herein may be used as modifications of the methods described in GB 1004709.0. Detection methods used may be of the kind that require the presence of viable micro-organisms, such as culturing.

Micro-organisms and/or fragments that may be captured according to the invention include bacteria, viruses, fungal cells, animal cells and plant cells and their cell components.

The invention will be further described and illustrated by the following specific examples.

Example 1

Demonstration of Organisms Binding to Different Bead Types

Rationale

Overnight cultures of *Escherichia coli*, *Staphylococcus aureus* and *Candida glabrata* were used to investigate binding to various bead types under various conditions. Enough of each culture was used so that the solution was turbid and the binding and subsequent elution could be followed by eye.

Method 1. 10 ml of the bacterial cultures were centrifuged at 8,000×g for 5 min and resuspended in 10 ml distilled water to give a turbid suspension of organisms.
2. 500 µl of each suspension was diluted to 1 ml with either 1 M NaCl or 1 M NaCl, 20% (w/v) PEG 8000 (leading to a PEG concentration in the medium of 10%).
3. 25 µl of a suspension of various paramagnetic beads (about 1 mg beads) was added and incubated for 10 min.
4. The beads were pulled to the side of the tube using a magnetic rack and the supernatant removed.
5. The supernatant was observed for turbidity and for the presence of a pellet of organisms after centrifugation at 8,000×g for 5 min.
6. To elute the captured organisms, the beads were resuspended in 250 µl of 0.5 M NaCl and then placed back in the magnetic rack.
7. The supernatant was observed for turbidity and for the presence of a pellet of organisms after centrifugation at 8,000×g for 5 min.

Results

The results are shown in the next following table. The paramagnetic bead types used are listed below:
A. BioMag Amine beads (Bangs Laboratories, catalogue number BM546).
B. As in A but coated with pDADMAC.
C. As in B but overcoated with dextran sulphate.
D. Dynalbeads M-270 amine (Invitrogen).
E. Silicon carbide beads (50 microns) coated with pDADMAC
F. Silicon carbide beads (50 microns) uncoated

|  | Capture Condition | Bead type | Organisms captured (%) | Organisms eluted |
|---|---|---|---|---|
| *E. coli* | With PEG | A | 100% | Yes |
|  |  | B | 100% | Yes |
|  |  | C | 100% | Yes |
|  |  | D | 100% | Yes |
|  |  | E | <50% | Yes |
|  |  | F | <25% | Yes |
|  | Without PEG | A | 0 | NA |
|  |  | B | 0 | NA |
|  |  | C | 0 | NA |
|  |  | D | 0 | NA |
|  |  | E | 0 | NA |
|  |  | F | 0 | NA |
| *S. aureus* | With PEG | A | 100% | Yes |
|  |  | B | 100% | Yes |
|  |  | C | 100% | Yes |
|  |  | D | 100% | Yes |
|  |  | E | <50% | Yes |
|  |  | F | <25% | Yes |
|  | Capture Condition | Bead type | Organisms captured (%) | Organisms eluted |
|  | Without PEG | A | 0 | NA |
|  |  | B | 0 | NA |
|  |  | C | 0 | NA |
|  |  | D | 0 | NA |
|  |  | E | 0 | NA |
|  |  | F | 0 | NA |
| *Candida glabrata* | With PEG | A | 100% | Yes |
|  |  | B | 100% | Yes |
|  |  | C | 100% | Yes |
|  |  | D | 100% | Yes |
|  |  | E | <50% | Yes |
|  |  | F | <25% | Yes |
|  | Without PEG | A | 0 | NA |
|  |  | B | 0 | NA |
|  |  | C | 0 | NA |
|  |  | D | 0 | NA |
|  |  | E | 0 | NA |
|  |  | F | 0 | NA |

NA, not applicable. There was no capture and no organisms to elute.
<50% indicates 25%-50% binding Discussion All organisms (the gram positive and gram negative bacteria and the fungi) were captured in the presence of 10% (w/v) PEG to all bead types tested though the capture to silicon carbide beads was less efficient. The capture to the paramagnetic beads in the presence of PEG was very efficient; the supernatant after capture had no turbidity and had no observable organism pellet post-centrifugation. Similarly, the eluate was turbid and had an observable organism pellet post-centrifugation which was similar in size to the comparable culture volume that had not been through the capture and elute process. Without PEG in the capture there was no capture of organisms and all of the organisms remained in the supernatant. The lesser degree of capture to pDADMAC when coated on silicon carbide in comparison to paramagnetic beads may be due to differences in the efficiency of the coating.

Example 2

Investigating the Requirement for NaCl in the PEG Capture

Rationale.

In this example, the *E. coli* was concentrated using carboxy paramagnetic beads (Invitrogen) in buffers containing different combinations of PEG and NaCl.

Method

Enough of an overnight culture of *Escherichia coli* was used so that the solution was turbid and the binding could be followed by eye.

Method 1. 10 ml of the bacterial cultures were centrifuged at 8,000×g for 5 min and resuspended in 10 ml distilled water to give a turbid suspension of organisms.
2. 500 µl of each suspension was diluted to 1 ml with either 1 M NaCl or 1 M NaCl, 20% (w/v) PEG 8000 or 20% (w/v) PEG 8000.
3. 100 µl (about 0.4 mg beads) of a suspension of carboxy paramagnetic beads (Invitrogen) was added and incubated for 10 min.
4. The beads were pulled to the side of the tube using a magnetic rack and the supernatant removed.
5. The supernatant was observed for turbidity and for the presence of a pellet of organisms after centrifugation at 8,000×g for 5 min.

Results

| Binding buffer used | Extent of capture (%) |
|---|---|
| 0.5 M NaCl | 0 |
| 0.5 M NaCl, 10% (w/v) PEG 8000 | 100 |
| 10% (w/v) PEG 8000 | 25 |

Discussion

Bacteria in general are negatively charged and would be repelled by the negatively charged carboxy beads. Such repulsion may aid removal of the bacteria from the beads at a later stage. In the absence of PEG (NaCl only) there is no binding of the *E. coli* to the beads. With PEG alone there is some binding but the efficiency is increased by the presence of NaCl which presumably helps to sequester the negative charges both on the bacilli and on the beads and thus promotes bacteria binding to the beads.

Example 3

Concentration of *Mycobacterium tuberculosis* from Sputum Using Paramagnetic Beads Rationale.

In this example, the *Mycobacterium tuberculosis* (TB) was concentrated from thinned sputum which has a high pH using beads (BioMag Amine beads, Bangs Laboratories, catalogue number BM546) coated with poly diallyl dimethyl ammonium chloride (pDADMAC). The presence of TB on the beads was then confirmed by acid fast microscopy.

Method

For comparison, sputum samples were thinned with sodium hydroxide, N-acetyl cysteine then split and one half processed by the bead capture and the other half processed by routine laboratory procedure which included centrifugation concentration of the bacilli and auramine staining of the deposits.

The Bead Capture Protocol
1. The sputum was thinned following standard laboratory procedure by adding an equal volume of 0.5 M NaOH, 2% (w/v) N-acetyl cysteine.
2. Samples were left for 10 min.
3. 2 ml of the thinned sputum was then added to an equal volume of 20% PEG 8000, 3M NaCl and 80 µl of the pDADMAC coated beads (about 5 mg of beads) was added and incubated for 10 min. (note: the sample was not neutralised prior to this step and the capture occurred at high pH measured at 14 using pH paper).
4. The beads were then collected using a magnet and the supernatant removed.
5. The beads were resuspended in 1 ml PBS containing 0.75M NaCl and again collected on a magnet.
6. The supernatant was removed and the beads resuspended in 50 µl PBS before spreading onto a glass microscope slide and drying.
7. The slide was stained with auramine O for acid fast mycobacteria using a standard protocol.

Results 10 sputum samples were tested. 6 of the samples were positive by microscopy by both methods (i.e. the traditional centrifugation concentration method and the bead capture method). 4 samples were negative by microscopy by both methods. There was, therefore, 100% correlation between the two methods.

Discussion

This example demonstrates that the TB can be captured from the sputum under alkali conditions and that the method is comparable in its effectiveness to the traditional method of concentration by centrifugation.

Example 4

Concentration of *Mycobacterium tuberculosis* from Sputum Using Settling Beads

Rationale.

In this example, the *Mycobacterium tuberculosis* (TB) is concentrated from thinned sputum which has a high pH using 50 micron silicon carbide beads either uncoated or coated with poly diallyl dimethyl ammonium chloride (pDADMAC). The capture of TB was then confirmed by acid fast microscopy.

Method

For comparison, sputum samples were thinned with sodium hydroxide, N-acetyl cysteine then one half processed by the uncoated beads and the other half processed by the coated beads.

The Bead Capture Protocol
1. The sputum was thinned following standard laboratory procedure by adding an equal volume of 0.5 M NaOH, 2% (w/v) N-acetyl cysteine.
2. Samples were left for 10 min.
3. 2 ml of the thinned sputum was then added to an equal volume of 20% PEG 8000, 3M NaCl and 200 µl of a 50% suspension of coated or uncoated silicon carbide beads added and mixed. (note: the sample was not neutralised prior to this step and the capture occurred at high pH measured at 14 using pH paper).
4. After the beads had settled by gravity they were washed by resuspension in 1M Tris pH 7.5 and allowed to settle once more.
5. The beads were finally washed in PBS and after settling the supernatant was removed.
6. Captured bacilli were eluted by addition of 50 µl chloroform and vortexing.
7. After allowing the beads to settle, the liquid supernatant was removed and spotted onto a microscope slide.
8. After drying, the slide was stained with auramine O for acid fast mycobacteria using a standard protocol.

Results 4 sputum samples that were positive for mycobacteria using standard acid-fast direct smear were tested. After processing by both the uncoated and coated beads, all samples were found to be positive by microscopy.

Discussion

This demonstrates that mycobacteria can be captured from thinned sputum at high pH using coated or uncoated silicon carbide beads and high concentrations of PEG.

Example 5

Concentration of *Mycobacterium tuberculosis* from Sputum

Rationale.

In this example, the *Mycobacterium tuberculosis* (TB) is concentrated from the sputum in a two-step procedure. First, the TB is concentrated by centrifugation and the pellet from this step is captured onto beads in the presence of high salt and PEG8000. The presence of TB on the beads is then confirmed by acid fast microscopy.

Method
1. Direct smears were prepared from sputum and stained by auramine O by a standard method. The slides were then investigated by fluorescent microscopy for the presence of fluorescent mycobacteria.
2. An equal volume of 1 m NaOH, 2% N-acetyl cysteine was added to the remaining sputa and mixed with occasional shaking for 20 min.
3. The sputa were then centrifuged at 4,000×g for 20 min.
4. The pellets were resuspended in 0.5 ml 100 mM sodium phosphate buffer pH 7.5 and 0.5 ml 1 M NaCl, 20% (w/v) PEG8000 added and mixed followed by 100 µl of beads of type B as defined in example 1.
5. After 10 min, the beads were collected on a magnet and resuspended in 50 µl 1 M NaCl.
6. The beads were spread onto a glass slide and the slide stained by auramine O for acid fast mycobacteria using a standard protocol.

Results

All samples positive by direct smear were also positive after centrifugation and bead-binding. In addition, in comparison to direct smear, there were many more bacilli per microscopy field which demonstrates that the TB had been concentrated from the sample.

Discussion

This example demonstrates the two step concentration of TB from sputum. The first step involved centrifugation which concentrated the TB into a 1 ml volume. This volume was too large to be applied directly to a microscope slide so the TB was further concentrated by bead capture to a volume that was small enough to be applied to a slide for microscopy.

Example 6

Concentration of *Mycobacterium tuberculosis* from Sputum Under Different Bead Coating and Binding Conditions Rationale.

In this example, different bead coating and binding conditions and were investigated for the capture and concentration of *Mycobacterium tuberculosis* (TB) from sputum prior to microscopy.

Method

1. An equal volume of 1M NaOH, 2% N-acetyl cysteine was added to smear positive sputum and incubated for 10 min to thin the sputum.
2. 0.5 ml aliquots of sputum were then either processed a) directly by addition of an equal volume of 20% PEG 8000 and 100 μl of BioMag Amine beads (Bangs Laboratories, catalogue number BM546) coated with polybreen or b) centrifuged, the pellet washed in 1 M Tris pH 7 and resuspended in 1 ml 1M Tris pH 7.0, 1 M NaCl, 10% PEG 8000 with the addition of 100 μl polybreen-coated beads. As a control, 0.5 ml of beads was processed with PEG 8000 and pDADMAC-coated beads as described in Example 5.
3. After 10 min, the beads were collected on a magnet and resuspended in 1 ml 10×PBS.
4. The beads were collected on a magnet again and resuspended in 50 μl 5×PBS and spread onto a glass slide and the slide stained by auramine 0 for acid fast mycobacteria using a standard protocol.

Results

All methods demonstrated capture of mycobacteria. The numbers of mycobacteria captured using polybreen-coated beads in the presence of PEG at high pH was almost equivalent to the control capture. The numbers of mycobacteria captured using polybreen-coated beads in the presence of high salt at neutral pH was slightly reduced compared to the control capture.

Discussion

This example demonstrates that polybreen-coated beads can be used to capture mycobacteria from sputum.

Example 7

Demonstration of Capture of Non-Sedimentable Fragments of Micro-Organisms

Rationale

In this example, whole intact mycobacteria were removed from thinned sputum by centrifugation. The supernatant was then tested to show that the non-sedimentable fragments of mycobacteria could be captured and concentrated by beads in the presence of PEG 8000.

Method

1. Sputum samples that were smear-positive and smear-negative for mycobacteria were thinned following standard laboratory procedure by adding an equal volume of 0.5 M NaOH, 2% (w/v) N-acetyl cysteine.
2. Samples were left for 10 min.
3. 1 ml of the thinned sputum was then centrifuged at 13,000×g for 5 min and the supernatant removed.
4. 0.7 ml of the supernatant was added to 0.7 ml 20% PEG 8000, 3M NaCl and 100 μl of a 50% suspension of uncoated 50 micron silicon carbide beads added and mixed.
5. After the beads had settled by gravity they were washed by resuspension in 1M Tris pH 7.5 and allowed to settle once more.
6. The beads were finally washed in PBS and after settling the supernatant was removed.
7. The non-sedimentable micro-organism fragments were eluted from the beads by adding 50 μl of lysis beads (lysis matrix B beads from Fischer Scientific) and disruption for 5 min at 2800 rpm on a Disruptor Genie (Scientific Industries).
8. 100 μl of each eluate was analysed directly by a commercially available microplate LAM ELISA (Clearview, Invernesss Medical) that recognises antigens specific for *Mycobacteria*.

Results

| Sample analysed | Absorbance 450 nm* |
|---|---|
| Microscopy positive sputum supernatant | 2.20 |
| Microscopy negative sputum supernatant | 0.00 |

*readings after subtraction of conjugate control blanks

Discussion

The silicon carbide beads in the presence of 10% PEG were able to capture and concentrate the non-sedimentable fragments of mycobacteria that could then be detected by ELISA.

Example 8

Concentration of *Mycobacterium tuberculosis* from Sputum Using Different Polymers and Magnetic Beads Composed of Magnetite Rationale Different polymers of different structures were tested. The following were included: Polyvinylpyrrolidone of average molecular weight 10,000; Polyethylene glycol of average molecular weight 200; Polyethylene glycol of average molecular weight 8000 (all supplied by Sigma Aldrich, USA).

Method
1. The different polymers were each made up to a 15% solution containing 1.5 M NaCl and 2% magnetite beads, <5 μm diameter (Sigma Aldrich USA, 310069-500G, Iron II,III oxide powder).
2. A sputum sample that was positive by microscopy for acid fast *Mycobacterium tuberculosis* was thinned with an equal volume of 0.5M NaOH for 10 min then aliquotted into 2 ml aliquots
3. To these aliquots was added an equal volume of a polymer solution which was mixed with the thinned sputum and left for 2 min
4. The beads were then captured on a magnet and the liquid removed
5. After removal from the magnet, the beads were washed by resuspension in 10 ml 10 mM NaOH.
6. After placing back on the magnet, the 10 mM NaOH was removed and any captured TB was eluted by resuspension of the beads in 100 μl Elution Buffer (100 mM Phosphate buffer pH 7.0, 0.5% N-lauroyl sarcosine).
7. After removal of the beads using the magnet, 50 μl of the supernatant was investigated by standard acid-fast microscopy.

Results

The numbers of TB bacilli per microscopy field were estimated after capture from the thinned sputum using the different solutions of polymer (see table below). Although polyethylene glycol of high molecular weight (about 8000) appeared to work best, the lower molecular weight polyethylene glycol also worked well. The polymer, polyvinylprrolidone also worked well

| | |
|---|---|
| Polyvinylpyrrolidone (average molecular weight 10,000) | 23 |
| Polyethylene glycol (average molecular weight 200) | 22 |
| Polyethylene glycol 8000 (average molecular weight 8000) | 33 |
| No polymer control | 6 |
| Direct smear (no concentration) | 8 |

Conclusion

A number of polymers were able to concentrate the TB from the sputum when compared to the no polymer control and the direct smear (microscopy without concentration). This experiment demonstrates that different polymers of differing chemical structure and differing molecular weights can be effective for concentration of TB from sputum in conjunction with the magnetite beads.

Example 9

Demonstration of the Capture of Soluble Fragments of Bacilli

Rationale

We have previously demonstrated the capture of intact bacilli. In this experiment we removed intact bacteria from a clinical sample by high-speed centrifugation, a method known to sediment bacteria, and then used polyethylene glycol 8000 (PEG 8000) and magnetite beads to capture the soluble fragments from the supernatant. The presence of these soluble bacterial fragments is demonstrated by ELISA after elution from the beads.

Method

1. Sputum samples were investigated by standard acid-fast microscopy for the presence of mycobacteria. A positive and a negative sputum were selected and treated with sodium hydroxide in a standard way in order to thin the sputum.
2. 1 ml of each sample was then centrifuged at high speed; 13,000×g for 10 min which exceeds the centrifugal force of 4000×g which is usually used to sediment bacteria.
3. The supernatant was removed for testing and the pellets were also resuspended in 1 ml PBS for further testing.
4. Bacteria and bacterial fragments in the samples were extracted by addition of an equal volume of 15% polyethylene glycol 8000, 1.5 M NaCl, 2% magnetite beads. After mixing and incubation for 2 min the beads were collected on a magnet and the supernatant removed.
5. The beads were resuspended in 10 mM NaOH and recaptured on the magnet.
6. The 10 mM NaOH was removed and the beads were resuspended in 100 μl Elution Buffer (100 mM Phosphate buffer pH 7.0, 0.5% N-lauroyl sarcosine).
7. The beads were removed using a magnet and 100 μl of eluate tested for the presence of mycobacterial lipoarabinomannan (LAM) by a standard ELISA procedure. The presence of LAM which is a mycobacterial cell wall component acts as a marker for the presence of bacterial cell wall fragments.

Results

As expected, the extracted supernatant and pellet from the negative sputum that did not contain mycobacteria gave no ELISA signal. In contrast there was an ELISA signal from the extracted mycobacteria-positive sputum in both the supernatant and pellet (see table below).

| Sample analysed | ELISA Reading (OD450 nm) |
|---|---|
| Microscopy positive sputum supernatant | 2.05 |
| Microscopy positive sputum pellet | 0.78 |
| Microscopy negative sputum supernatant | 0.00 |
| Microscopy negative sputum pellet | 0.07 |

Conclusion

The combination of PEG 8000 and magnetite was able to extract a LAM ELISA signal from the supernatant from which intact bacteria had been removed by centrifugation. This demonstrates that the PEG/magnetite procedure can be used to extract bacterial cell wall fragments from samples. Interestingly, with the positive sputum sample, the signal from the supernatant was higher than the signal from the pellet suggesting that a large proportion of the extractable mycobacterial components in sputum are in a soluble form.

Example 10

Investigation of the Extraction of Soluble Bacterial Components Spiked into Urine Rationale In this experiment we wished to demonstrate that PEG 8000 in combination with magnetite could be used to extract soluble mycobacterial components from urine as measured by an anti-lipoarabinomannan (LAM) ELISA.

Method
1. 1 ml of a culture of the mycobacteria Bacillus Calmette-Guérin (BCG) was centrifuged at 13,000×g for 5 min and 50 µl of the supernatant spiked into 2 ml urine.
2. The spiked urine and a non-spiked control urine were extracted by addition of an equal volume of 15% polyethylene glycol 8000, 1.5 M NaCl, 2% magnetite beads. After mixing and incubation for 2 min the beads were collected on a magnet and the supernatant removed.
3. The beads were resuspended in 10 mM NaOH and recaptured on the magnet.
4. The 10 mM NaOH was removed and the beads were resuspended in 100 µl Elution Buffer (100 mM Phosphate buffer pH 7.0, 0.5% N-lauroyl sarcosine).
5. The beads were removed using a magnet and 100 µl of eluate tested for the presence of LAM by a standard ELISA procedure. The presence of LAM which is mycobacterial cell wall component, acts as a marker for the presence of bacterial cell wall fragments.

Results

| Sample analysed | ELISA Reading (OD450) |
|---|---|
| BCG culture supernatant added to urine | 1.03 |
| Urine control | 0.00 |

Conclusion

The combination of PEG 8000 and magnetite beads was able to extract the soluble BCG components that had been spiked into urine.

Example 11

Demonstration of the Capture of Virus

Rationale

The PEG/magnetite extraction system can extract bacteria, fungi and soluble bacterial components. In this experiment we show that it can also extract viruses.

Method
1. Various amounts of Adenovirus were diluted in 250 µl H20.
2. An equal volume of 30% PEG 8000, 3M NaCl, 4% magnetite was added and mixed.
3. After 10 min the magnetite beads were washed twice with 0.5 ml 7.5% PEG 8000, 0.5M NaCl using a magnet.
4. Finally, the beads were resuspended in 20 µl PBS 0.1% Triton X-100 to elute the captured virus.
5. After removal of the beads using a magnet 2 µl of eluate was analysed by PCR using primers: AdF, 5' GGA CGC CTC GGA GTA CCT GAG 3' and AdR, 5' ACC GTG GGG TTT CTA AAC TTG TT 3'

Results

The PCR cycle at which each reaction became positive (ct value) is shown in the table.

| Amount of Adenovirus added (ng/ml) | PCR Ct |
|---|---|
| 300 | 23 |
| 30 | 26 |
| 3 | 28 |
| 0.3 | No Ct |
| 0 | No Ct |

3 ng/ml of Adenovirus could be detected which equates to 0.75 ng in the sample volume tested.

Conclusion

The Adenovirus was captured from solution by the combination of PEG8000 and magnetite and was retained on the bead through two washes prior to elution and detection by PCR.

To provide a solution to the problem of a generic approach to the concentration of a widest range of micro-organisms and fragments thereof including gram positive and negative bacteria, mycobacteria and fungi from large sample volumes that may include harsh conditions of pH or salt concentrations we have developed an improved method that involves the use of polyethylene glycol and similar substances to deposit the microorganisms or fragments onto the surface of a capture matrix. The use of polyethylene glycol removes the dependency of capture on the nature of the surface of the capture matrix and we have shown that many different capture matrices of many different surface natures can be used to capture a range of microorganisms and fungi.

It is our observation that all bacteria and fungi tested, including gram negative and gram positive bacteria can be bound to surfaces, such as charged paramagnetic beads in the presence of a water soluble polymer, such as polyethylene glycol (PEG). Polyethylene glycols of many different sizes can be used. In addition, many different types of beads can be used including those with a carboxy, amine, pDADMAC, or dextran sulphate coating, or beads can be used directly without coating. The beads can be paramagnetic, ferromagnetic (including ferrimagnetic), or simple silicon carbide or aluminium oxide but particularly useful embodiments for most bacilli and fungi use paramagnetic beads with a carboxy surface, or uncoated silicon carbide beads, or uncoated magnetite beads.

If using paramagnetic or ferromagnetic bead surfaces the microorganisms can be concentrated using a magnet to remove the beads from suspension and then eluted in a small volume of buffer with reduced or no polyethylene glycol content. Similarly, if using silicon carbide beads that sediment under gravity the microorganisms can be concentrated and eluted, after bead settling, in a small volume of buffer with reduced or no polyethylene glycol content.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A method of capturing onto a solid surface micro-organisms and/or fragments of micro-organisms present in an aqueous liquid, comprising adding to said liquid a sufficient quantity of a water soluble polymer in the presence of said solid surface to displace said micro-organisms and/or fragments from the liquid to the solid surface.

2. A method as claimed in claim 1, wherein the concentration of the added water soluble polymer in the aqueous liquid is from 2 to 40% w/v.

3. A method as claimed in claim 2, wherein said concentration is from 5-15% w/v.

4. A method as claimed in claim 1, in which the water soluble polymer is a non-ionic hydrophilic polymer.

5. A method as claimed in claim 4, in which the water soluble polymer is a dextran, PVP or PEG.

6. A method as claimed in claim 1, wherein the water soluble polymer has a molecular weight of from 1,000 to 20,000.

7. A method as claimed in claim 6, wherein the water soluble polymer has a molecular weight of from 5,000 to 13,000.

8. A method as claimed in claim 1, wherein the ionic strength of the aqueous liquid is raised by the addition of a water soluble inorganic salt to from 150 mM to 6M.

9. A method as claimed in claim 8, wherein said salt concentration is from 0.25 to 2.5M.

10. A method as claimed in claim 1, wherein the solid surface is provided by beads.

11. A method as claimed in claim 10, wherein said beads are paramagnetic, ferromagnetic or have a density such that they separate on standing.

12. A method as claimed in claim 11, wherein the beads are of magnetite.

13. A method as claimed in claim 11, wherein the beads are of silicon carbide.

14. A method as claimed in claim 1, wherein the solid surface is of a polymer having positively charged or negatively charged surface groups.

15. A method as claimed in claim 14, wherein said surface groups are amine, quaternary ammonium, carboxylic acid, sulphonic acid, or sulphate groups.

16. A method as claimed in claim 1, further comprising separating said solid surface from said liquid.

17. A method as claimed in claim 16, further comprising eluting said micro-organisms and/or fragments from said solid surface after separation thereof from said liquid.

18. A method as claimed in claim 17, wherein the micro-organisms and/or fragments are eluted from the solid surface into a volume of liquid which is less than the volume of the liquid in which the micro-organisms and/or fragments were originally suspended by a factor of at least 2.

19. A method as claimed in claim 1, further comprising detecting the micro-organisms and/or fragments which were captured onto the solid surface.

20. A method as claimed in claim 19, further comprising identifying the micro-organisms and/or fragments which were captured onto the solid surface.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
    /note="primer for PCR"
    /organism="artificial sequences"

<400> SEQUENCE: 1
ggacgcctcg gagtacctga g                                    21

<210> SEQ ID NO 2
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
    /note="primer for PCR"
    /organism="artificial sequences"

<400> SEQUENCE: 2
accgtggggt ttctaaactt gtt                                  23